United States Patent [19]
Billington et al.

[11] Patent Number: 4,814,362
[45] Date of Patent: Mar. 21, 1989

[54] GLASSES AND POLY(CARBOXYLIC ACID) CEMENT COMPOSITIONS CONTAINING THEM

[75] Inventors: Richard W. Billington, London; Jill A. Williams, Thorpe, both of England

[73] Assignee: Dentsply Limited, England

[21] Appl. No.: 34,877

[22] Filed: Apr. 6, 1987

[30] Foreign Application Priority Data

Apr. 8, 1986 [GB] United Kingdom ............... 8608548

[51] Int. Cl.$^4$ .......................... C08K 3/40; A61K 6/08
[52] U.S. Cl. ................................................. 523/117
[58] Field of Search ....................................... 523/117

[56] References Cited

U.S. PATENT DOCUMENTS

| | | |
|---|---|---|
| 4,032,504 | 6/1977 | Lee, Jr. et al. |
| 4,215,033 | 7/1980 | Bowen. |
| 4,492,777 | 1/1985 | Denton, Jr. et al. |
| 4,527,979 | 7/1985 | McLean et al. .................... 523/118 |

FOREIGN PATENT DOCUMENTS

| | | |
|---|---|---|
| 3000118 | 9/1979 | Fed. Rep. of Germany. |
| 2246589 | 9/1974 | France. |
| 8000409 | 3/1980 | World Int. Prop. O. |

*Primary Examiner*—Herbert J. Lilling
*Attorney, Agent, or Firm*—Edward J. Hanson, Jr.; David E. Wheeler

[57] ABSTRACT

Alkaline earth metal aluminofluorosilicate glasses suitable for use as ion-sources in the poly(carboxylic acid) cement compositions contain strontium in order to provide radiopacity. The invention also provides methods for making poly(carboxylate) cement using the glasses of the invention as ion-sources.

10 Claims, No Drawings

GLASSES AND POLY(CARBOXYLIC ACID) CEMENT COMPOSITIONS CONTAINING THEM

This invention is concerned with improvements in and relating to acid-leachable glasses and to poly(carboxylic acid) cement compositions containing such glasses.

Poly(carboxylic acid) cement compositions are well known and established. Such compositions basically comprise (i) a polymer containing free carboxylic acid groups (typically a homo- or co-polymer of acrylic acid) and (ii) an acid leachable source of polyvalent metal ions (e.g. an acid leachable glass such as a calcium aluminofluorosilicate glass). In the presence of water, the polyacid leaches polyvalent metal ions from the source thereof and these serve to cross-link the polymer chains to give a solid material (a cement). Poly(carboxylic acid) compositions are discussed authoritatively in, for example, "Organolithic Macromolecular Materials" Wilson, A.D. Crisp, S.; Applied Science Publishers, 1977; see especially chapter 4.

Poly(carboxylic acid) cement compositions have been found to have particular application as dental restorative materials but suffer from one practical disadvantage in that they are radiolucent, that is they are essentially transparent to X-rays. As a result, it is not possible, for example, to examine a dental restoration, carried out using such a cement, using an X-ray technique and, further, it is not possible to locate any portion of a dental restoration which may become dislodged and ingested by a person, using an X-ray technique.

It has now been found, in accordance with the present invention, that at least a part, and preferably all, of the calcium in a calcium aluminofluorosilicate glass may be replaced by strontium to give a glass which may be used as an ion-source in a poly(carboxylic acid) cement composition to give a set material which is radiopaque, that is opaque to X-rays, and still has acceptable properties with regard to strength, hardness, translucency etc.

The set cement may have a radiopacity equal to or greater than that of natural tooth material. (The radiopacity of a material may be conveniently defined in terms of the equivalent thickness, in mm, of aluminium required to give the same radiopacity as one mm of the material. In these terms, the radiopacity of dental enamel is generally from 1.3 to 2.7 mm aluminium per 1 mm enamel; that of dentine being lower, about 0.6 to 0.9 mm aluminium per 1 mm dentine).

According to the invention, therefore, there is provided an alkaline earth metal aluminofluorosilicate glass, for use as an ion-source in a poly(carboxylic acid) cement composition, in which at least a part of the alkaline earth metal is strontium.

In order to achieve acceptable radiopacity in use, the glass suitably contains from 5 to 35% preferably from 5 to 24%, most preferably from 12 to 18% by weight, of strontium (calculated as SrO) and in order to achieve this it is most convenient that all the alkaline earth metal in the glass be strontium, i.e. that the glass be a strontium aluminofluorosilicate glass substantially free of other alkaline earth metals such as calcium.

The glasses of the invention may be prepared from a mixture of alumina, silica, aluminium fluoride, aluminium phosphate and strontium fluoride (in place of calcium fluoride) in the presence of, for example cryolite (sodium aluminium fluoride) or boric acid as fluxing agents. Thus, preferred glasses of the invention comprise: strontium (calculated as SrO), 8 to 32% by weight; aluminium (calculated as $Al_2O_3$), 25 to 40% by weight; silica (calculated as $SiO_2$), 23 to 33% by weight; fluorine (calculated as $F_2$), 0 to 10% by weight; sodium (calculated as $Na_2O$), 1 to 7% by weight; and phosphorus (calculated as $P_2O_5$) 0 to 10% by weight.

As noted above, the glasses of the invention are suitable for use as ion-sources in poly(carboxylic acid) cement compositions and, accordingly, the invention further provides a method of producing a cross-linked poly(carboxylate) cement which comprises reacting a polymer containing free carboxyl groups with a particulate glass of the invention, in the presence of water.

The polymer containing free carboxyl groups is preferably a homopolymer of acrylic acid. Copolymers of acrylic acid with one or more other ethylenically unsaturated carboxylic acids such as maleic or itaconic acid, may be employed but are less preferable. The acrylic acid polymer or copolymer suitably has a molecular weight of from 20,000 to 125,000, preferably from 35,000 to 70,000, most preferably from preferably 45,000 to 75,000. For the sake of convenience the polymer containing free carboxylic acid groups will hereinafter simply be referred to as a "polyacrylic acid".

The glass should be in particulate form and suitably has a particle size of from 0.5 to 60 $\mu$m. The particle size of the glass may vary within these limits depending upon the intended end use of the poly(carboxylic acid) cement composition. Thus, for example, where the resin is to be used as a dental restorative material (i.e. as a filling or stopping material) or as a base under an amalgam or a so-called "composite" dental restorative material (i.e. a mixture of an ethylenically unsaturated resinous material, an inert particulate filler and a curing agent for the resinous material), the particle size is suitably 0.5 to 60 $\mu$m; preferably 1 to 40 $\mu$m and most preferably from 5 to 25 $\mu$m.. When intended for use as a luting agent the particle size is suitably 0.5 to 30 $\mu$m, preferably 0.5 to 25 $\mu$m and most preferably 1 to 20 $\mu$m.

The weight ratio of polyacrylic acid to glass is suitably from 0.15 : 1 to 0.5 : 1, preferably 0.2 : 1 to 0.4 : 1; and the weight ratio of water to glass is preferably 0.4 : 1 to 0.1 : 1.

The reaction of the polyacrylic acid and glass may be carried out in the presence of other materials serving to alter or modify the working time and/or setting time of the mixture, e.g. a hydroxycarboxylic acid such as tartaric acid serves to increase the rate of set of the composition.

Compositions for forming a cement from the glass of the invention and polyacrylic acid may be put up as two-part packs, one part comprising an aqueous solution of the polyacrylic acid (and optionally working/setting time modifiers) and the other part comprising a particulate glass. Alternatively, a dry blend may bee formed of particulate glass and a powdered polymer for subsequent addition of water to form a cement-forming composition. In this latter case working/setting time modifiers may be present in the dry blend or in the water.

The glasses of the invention may also be used to impart radiopacity to other polymerized resinous materials and thus a further aspect of the invention provides a radiopaque composition comprising a polymerised resinous material containing such a glass as a filler. Such a composition may suitably be a so-called "composite" dental restorative material, i.e. some derived from the polymerization of a composition comprising one or more ethylenically unsaturated monomers, a particular filler and a polymerization initiator for the ethylenically unsaturated monomer(s) which typically comprise acrylate monomers, that is esters of acrylic or methacrylic acid.

In a broader aspect the invention provides a polymer structure which is radiopaque and contains strontium as radiopaquing agent. Such a structure is preferably translucent and suitably has a radiopacity of at least 1 mm of aluminium per mm of structure, preferably at least 1.5 mm, and more preferably at least 2.0 mm, of aluminium per mm of structure.

In order that the invention may be well understood the following Examples are given by way of example only. In the Examples all percentages are by weight unless otherwise stated.

Example 1

A glass was prepared by fusing together 14.8% aluminium oxide, 25.9% silica, 3.3% strontium fluoride, 4.8& aluminium fluroide, 21.3% aluminium phosphate and 20.0% cryolite. The resultant glass (which contained 10.8% of strontium calculated as strontium oxide) was ground to a Sauter Mean Diameter of 2.5 $\mu$m and was blended with polyacrylic acid (molecular weight 45,000) and tartaric acid to give a cement-forming powder containing 83.6% of the glass, 15.1% of polyacrylic acid and 1.3% of tartaric acid.

The powder was subsequently mixed by hand, using a dental spatula and a glass block, with water (water:powder ratio=0.15:1) to give a restorative material (cement). This virtually translucent cement typically had a working time of 1 minute and 45 seconds from the start of mixing, a compressive strength, after 24 hours, of 250 MPa and a radiopacity of 1.2 mm aluminium per 1 mm cement.

Example 2

A glass was prepared by fusing 16.6% of aluminium oxide, 29.0% of silica, 34.3% of strontium fluoride, 5.3% of aluminium fluoride, 9.9% of aluminium phosphate and 5.0% of cryolite.

The resultant glass (which contained 29.2% of strontium calculated as strontium oxide) was used to prepare a cement-forming powder by blending it with the same polyacrylic acid as used in Example 1 and tartaric acid in the same proportions as used in Example 1. The powder was evaluated as described in Example 1 and it was found that the cement typically has a working time of 1 minute and 50 seconds from the start mix, a compressive strength after 24 hours of 245 MPa and a radiopacity of 2.8 mm aluminium per mm cement.

Example 3

A cement-forming powder was prepared from the glass of Example 2, the polyacrylic acid of Example 1 and tartaric acid; the cement containing 74.4% of the glass, 24.8% of the polyacrylic acid and 0.8% of the tartaric acid.

The powder (which was intended for use as a luting cement) was evaluated as described in Example 1 (at a powder:water ratio of 3.4:1) and typically had a working time of 3 minutes, a compressive strength of 90 MPa and a radiopacity of 2.2 mm aluminium per 1 mm cement.

We claim:

1. A method of preparing a radioopaque cross-linked poly (carboxylate) dental cement comprising the steps of:
    (a) preparing glass using components wherein strontium provides substantially all radioopaque properties in said glass, said glass being suitable as a fluoride ion source in said cement
    (b) blending said glass with 20,000 to 125,000 molecular weight polyacrylic acid to provide a powder blend of glass and polyacrylic acid
    (c) mixing said blend of glass and polyacrylic acid with water to produce a dental cement having a radiopacity at least substantially equivalent to that of dentin or dental enamel.

2. The method of claim 1 which comprises preparing said glass to consist essentially of by weight about 5-35% SrO, 25-40% Al$_2$O$_3$, 23-33% SiO$_2$, 0-10% F$_2$, 1-7% Na$_2$O, and 0-10% P$_2$O$_5$.

3. The method of claim 1 which comprises providing said polyacrylic acid as a homopolymer of acrylic acid having a molecular weight of 35,000-70,000.

4. The method of claim 1 in which said glass is pulverized, ground, and/or milled to have a particle size of from 0.5 to 60 $\mu$m.

5. The method of claim 1 which comprises blending said glass and said polyacrylic acid in a weight ratio of polyacrylic acid to glass of from 0.12:1 to 0.4:1 and the weight ratio of water to glass is 0.4:1 to 0.1:1.

6. The method of claim 1 which comprises the further step of including a hydroxycarboxylic acid in the mixing step, said hydroxycarboxylic acid serving to alter or modify the working time or setting time of the cementing reaction or both.

7. The method of claim 6 which comprises using tartaric acid to decrease the setting time of the reaction.

8. The method of claim 1 in which said glass is prepared to be substantially free of alkaline earth metals other than strontium.

9. The method of claim 1 which comprises adding strontium fluoride to said glass composition in preparing said glass, said fluoride acting as a leachable ion, and strontium acting as radioopacifying agent.

10. The method of claim 1 which produces a dental cement having a radioopacity of about 0.6 to 2.8 mm aluminum per mm of cement.

* * * * *